(12) United States Patent
Migita (10) Patent No.: US 8,641,623 B2
(45) Date of Patent: Feb. 4, 2014

(54) ULTRASONIC DIAGNOSTIC DEVICE

(75) Inventor: Manabu Migita, Kanagawa (JP)

(73) Assignee: Panasonic Corporation, Osaka (JP)

( * ) Notice: Subject to any disclaimer, the term of this patent is extended or adjusted under 35 U.S.C. 154(b) by 648 days.

(21) Appl. No.: 12/493,466

(22) Filed: Jun. 29, 2009

(65) Prior Publication Data

US 2010/0022879 A1 Jan. 28, 2010

(30) Foreign Application Priority Data

Jun. 30, 2008 (JP) .................................. 2008-170089

(51) Int. Cl.
*A61B 8/00* (2006.01)

(52) U.S. Cl.
USPC .......................................... 600/443; 600/437

(58) Field of Classification Search
None
See application file for complete search history.

(56) References Cited

U.S. PATENT DOCUMENTS

| 6,334,847 B1* | 1/2002 | Fenster et al. ................. | 600/443 |
| 2006/0250395 A1* | 11/2006 | Kwon et al. .................... | 345/424 |
| 2007/0167760 A1* | 7/2007 | Kim et al. ....................... | 600/437 |

FOREIGN PATENT DOCUMENTS

| JP | 10-337288 A | 12/1998 |
| JP | 2001-145631 A | 5/2001 |
| JP | 2005-157664 A | 6/2005 |

OTHER PUBLICATIONS

Japanese Office action for JP2008-170089 dated Sep. 7, 2012.

\* cited by examiner

*Primary Examiner* — James Kish
*Assistant Examiner* — Christopher Cook
(74) *Attorney, Agent, or Firm* — Pearne & Gordon LLP (57) ABSTRACT

The present invention provides ultrasonic diagnostic equipment for accurately determining a three-dimensional picture generation start depth, independently of a turbidity degree of an amniotic fluid and the like, which exist between a three-dimensional picture generation target such as an fetus and the like and a portion that is not the three-dimensional picture generation target such as a placenta or an uterine wall or the like serving as the obstacle of the fetus. In the present invention, the brightness values in the depth direction of an ultrasonic received signal are cumulated, and the depth direction of the ultrasonic received signal is divided into a plurality of depth zones S0 to S9 so that the respective cumulative addition values become the approximately same values, and among the depth zones S0 to S9, the plurality of higher depth zones having the longer zone length are selected as three-dimensional picture generation start candidate zones, and among the three-dimensional picture generation start candidate zones, the three-dimensional picture generation start candidate zone having the shallowest depth is selected as a three-dimensional picture generation start zone S, and a predetermined depth inside the three-dimensional picture generation start zone S is determined as a start depth A of the three-dimensional picture generation.

6 Claims, 10 Drawing Sheets

ULTRASONIC DIAGNOSTIC DEVICE

FIELD OF THE INVENTION

The present invention relates to ultrasonic diagnostic equipment that automatically determines a start depth of a three-dimensional picture generation and starts the three-dimensional picture generation.

BACKGROUND ART

As a three-dimensional ultrasonic picture generation technique in ultrasonic diagnostic equipment, a ray-casting method is well known. This method is widely used to draw a three-dimensional picture of a fetus, in a medical field (especially, an obstetrics and genecology department). Here, when in a case of drawing the three-dimensional picture of the fetus, the ray-casting method is simply used, the placenta and the uterine wall, which cover the fetus targeted for the three-dimensional picture generation although they are not targeted for the three-dimensional picture generation, are drawn which disables the three-dimensional picture of the desired fetus to be drawn. Thus, the conventional method was required to carry out a clipping operation in which a doctor or a sonographer manually removes the placenta and the uterine wall that shielded the fetus. This clipping operation was the technique whose automation was desired for a long time because the much labor and the long time were required for the doctor or sonographer.

Figure 7:
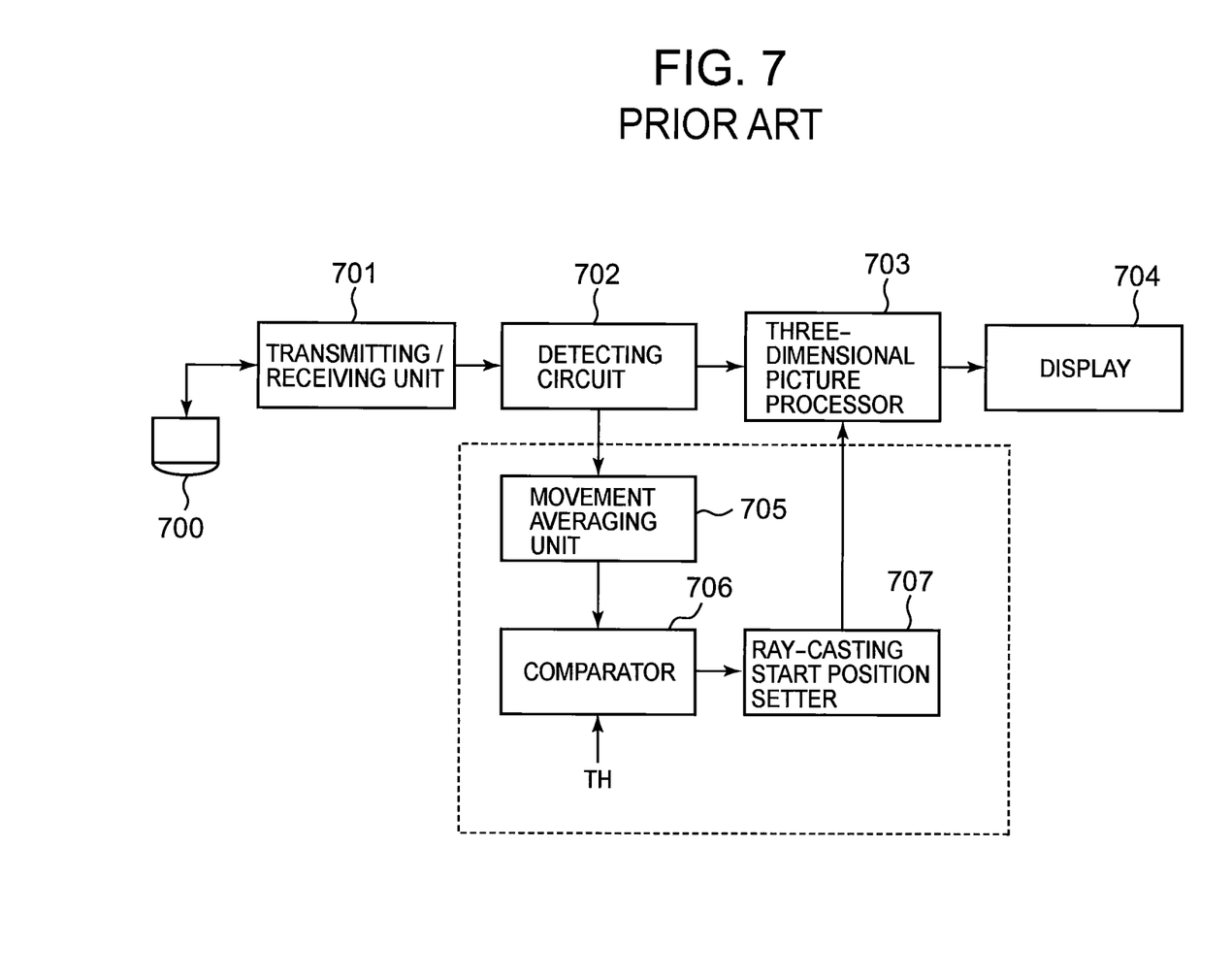
FIG. 7 is a block diagram in conventional ultrasonic diagnostic equipment.

So, an automatic obstacle removing method indicated by the following patent document 1 is proposed. FIG. 7 shows a block diagram of three-dimensional ultrasonic picture diagnostic equipment that contains a conventional automatic obstacle remover described in the patent document 1. In FIG. 7, a transmitting/receiving unit 701 transmits an ultrasonic beam through a two-dimensional array probe 700 to an object and receives a reflection wave from the object. A detecting circuit 702 detects a received signal from the transmitting/receiving unit 701. A three-dimensional picture processor 703 generates a volume data from the received signal from the detecting circuit 702 and carries out a ray-casting calculation and then generates a three-dimensional picture. A display 704 displays the three-dimensional picture generated by the three-dimensional picture processor 703. A movement averaging unit 705 smoothes the received signal processed by the detecting circuit 702. A comparator 706 compares the signal smoothed by the movement averaging unit 705 and a predetermined threshold TH to judge an amniotic fluid and then judges the drop portion of a received signal level. A ray-casting start position setter 707 determines a ray-casting start position in accordance with the drop portion (amniotic fluid portion) of the received signal level judged by the comparator 706 and outputs to the three-dimensional picture processor 703.

Figure 8:
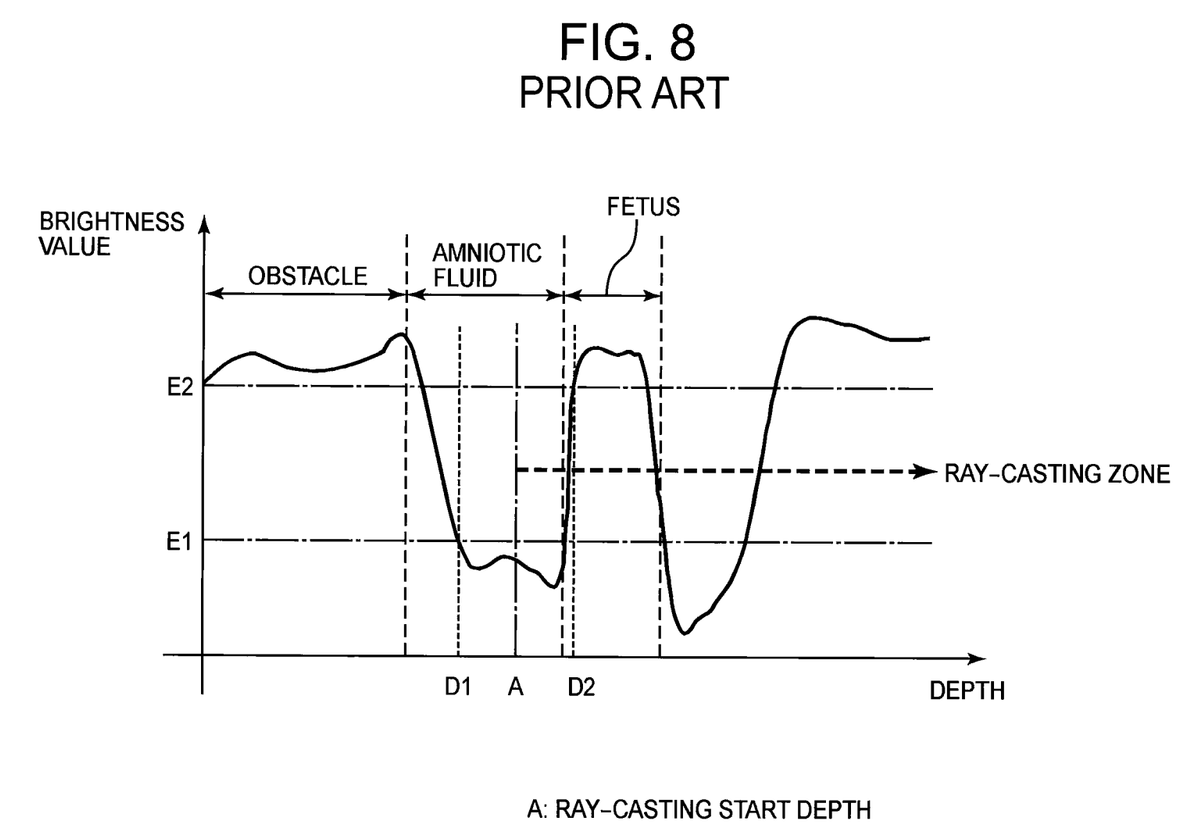
FIG. 8 is an explanatory view showing the conventional obstacle removing algorithm (A)

Here, the portion related to the automatic obstacle removal as the conventional technique is the portion surrounded by a dotted line in FIG. 7. This portion will be described below in detail. The comparator 706 can select two algorithms (A), (B) in order to detect the drop portion (amniotic fluid portion) in the depth direction of the received signal level. The algorithm (A) is the algorithm for detecting the drop portion in the depth direction of the received signal level (brightness value) in its original state, as shown in FIG. 8. The comparator 706 sequentially scans the received signal in the depth direction and stores a received signal depth D1 when the received signal becomes lower than the threshold TH=E1(<E2). Next, the comparator 706, while further advancing the scanning in the depth direction, stores a received signal depth D2 at this time when the received signal becomes higher than the threshold TH=E2. When the scanning of the received signal has been ended, the received signal depths D1, D2 are outputted to the ray-casting start position setter 707.

Figure 9:
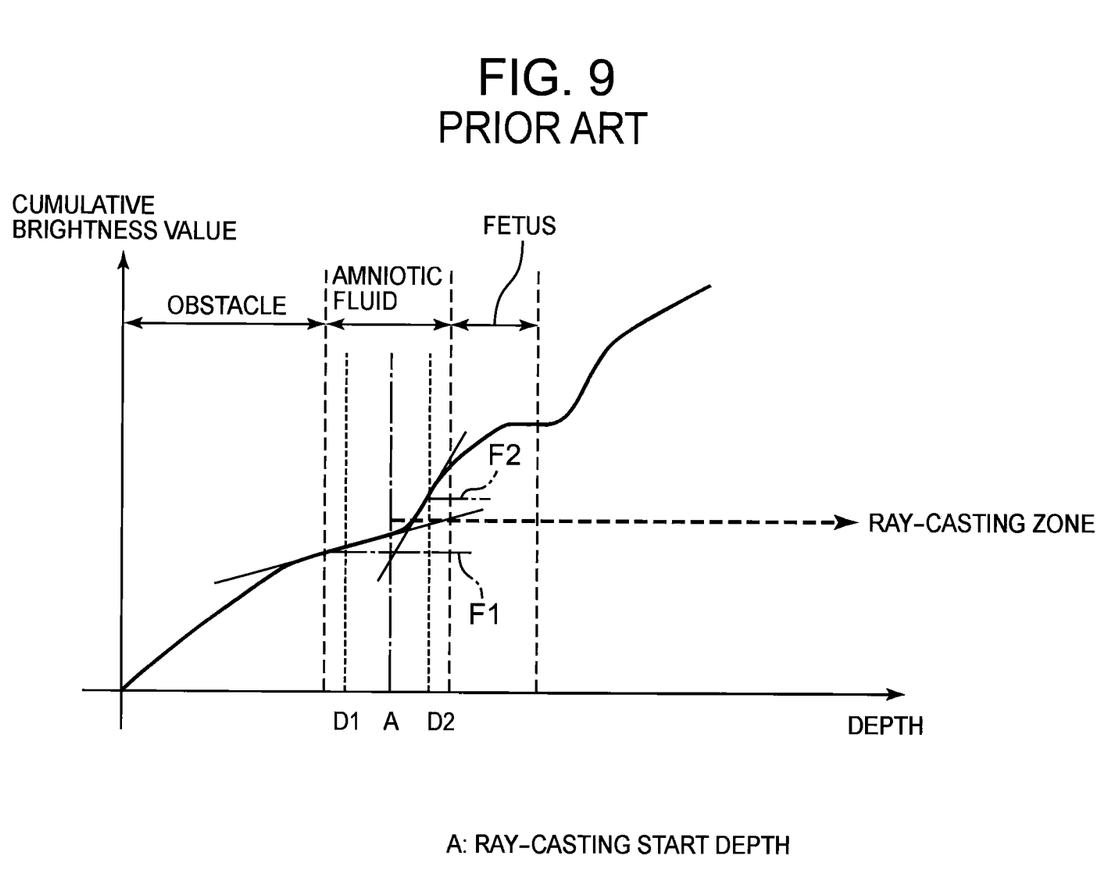
FIG. 9 is the explanatory view showing the conventional obstacle removing algorithm (B)

The algorithm (B) is the algorithm, which as shown in FIG. 9, integrates the received signal levels (brightness values) in the depth direction shown in FIG. 8, and determines a cumulative brightness value, and in accordance with the gradient (differential value) of the cumulative brightness values, indirectly detects the drop portion (amniotic fluid portion) in the depth direction of the received signal level. The comparator 706, before carrying out the comparing process, carries out the cumulative addition in the depth direction of the received signals. Next, the comparator 706 compares the previously-generated gradient in the cumulative addition with the thresholds TH=F1, F2 (F1<F2) and consequently determines the received signal depths D1, D2, similarly to the algorithm (A). At first, the comparator 706 sequentially scans the gradient of the cumulative addition value of the received signal in the depth direction and stores the received signal depth D1 when the gradient of the cumulative addition value of the received signal becomes smaller than the threshold TH=F1. Next, the comparator 706, while further advancing the scanning in the depth direction, stores the received signal depth D2 at this time when the gradient of the cumulative addition value of the received signal becomes greater than the threshold F2. When the scanning of the cumulative addition value of the received signal has been ended, the received signal depths D1, D2 are outputted to the ray-casting start position setter 707.

In the ray-casting start position setter 707, a middle depth= (D1+D2)/2 of the received signal depths D1, D2 determined by the comparator 706 is defined as a ray-casting start depth A, and outputted to the three-dimensional picture processor 703. For this reason, the three-dimensional picture processor 703 does not generate the three-dimensional pictures of the obstacles and a part of the amniotic fluid, which are located at the positions shallower than the ray-casting start depth A, and then generates the three-dimensional pictures of a part of the amniotic fluid and the fetus, which are located at the positions deeper than the ray-casting start depth A. As mentioned above, the conventional method, since containing the comparator 706 and the ray-casting start position setter 707, judges the drop portion of the received signal that serves as the amniotic fluid portion, and automatically removes the placenta, the uterine wall and the like (the obstacles) which cover the fetus, and consequently draws only the fetus.

Patent Document 1: Japanese Patent Application Publication (JP-P 2001-145631) (FIG. 4 and FIG. 6)

DISCLOSURE OF THE INVENTION

Figure 10A:
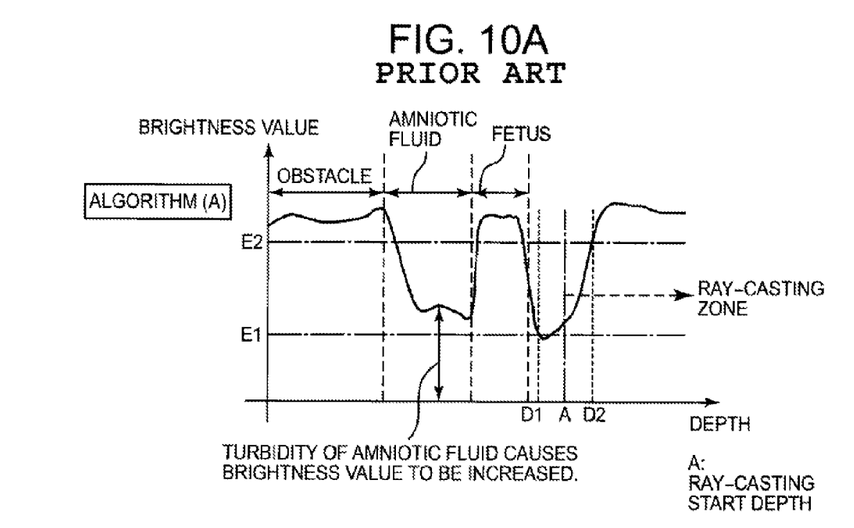
FIG. 10A is an explanatory view showing the problems to be solved by the present invention.
Figure 10B:
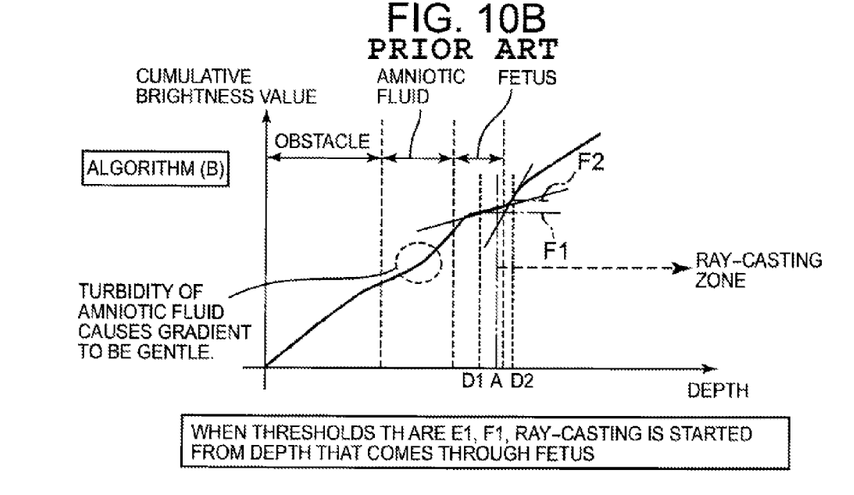
FIG. 10B is an explanatory view showing the problems to be solved by the present invention.

However, in the conventional configuration, the threshold levels TH=E1, E2 relative to the brightness curve in the depth direction for the comparator 706 or the thresholds TH=F1, F2 of the gradients relative to the cumulative addition brightness curve in the depth direction are required, thereby involving a necessity that those threshold parameters are optimized on the basis of the input received signal. For example, as shown in FIG. 10A, FIG. 10B, a case is assumed in which the amniotic fluid existing between the obstacle and the fetus is muddied by the bodily waste of the fetus and the like. By the way, we dare to describe that the amniotic fluid is typically muddied by the bodily waste of the fetus and the like and this fact cannot be ignored. Here, when the amniotic fluid is muddied, as shown in FIG. 10A, FIG. 10B, both of the brightness curve and cumulative addition brightness curve of the ultrasonic received signal do not become lower than the thresholds TH=E1 and TH=F1 in the portion of the amniotic fluid, and it is difficult to accurately specify the ray-casting start position A. Thus, in order to remove the obstacle, the suitable threshold is required to be determined on the basis of the muddy degree of the amniotic fluid.

Here, the nature of the threshold that serves as the obstacle removal condition is further discussed. The thresholds TH=E1, TH=F1 relative to the brightness curve and the cumulative addition brightness curve are the absolute parameters. Thus, they are the values that extremely depend on the brightness value and brightness change (curve differential value) in the curve. For this reason, the smoothing process of the curve is always required before the threshold is judged. Also, even if the smoothing process is carried out, this does not normally act as the threshold of the obstacle removal, when a certain degree of a bias is added to the curve or when the curve change is small. Thus, the employment of the brightness value itself or brightness value change as the threshold is considered not to be suitable.

The present invention is intended to solve the above-mentioned conventional problems and provide ultrasonic diagnostic equipment that can accurately determine the three-dimensional picture generation start depth, independently of the muddy degree of the amniotic fluid and the like that exist between the three-dimensional picture generation target, such as the fetus and the like, and the portion, which is not the three-dimensional picture generation target such as the placenta or uterine wall or the like, serving as the obstacle of the fetus.

In order to attain the above-mentioned objects, the present invention is ultrasonic diagnostic equipment for automatically determining the start depth of the three-dimensional picture generation and starting the three-dimensional picture generation, and this is configured by containing:

a divider which cumulates the brightness values in the depth direction of the ultrasonic received signal and divides the depth direction of the ultrasonic received signal into one or a plurality of depth zones so that the respective cumulative addition values become the approximately same values;

a start depth determiner in which among the one or plurality of depth zones divided by the divider, the plurality of higher depth zones having longer zone lengths are selected as three-dimensional picture generation start candidate zones, and among the plurality of three-dimensional picture generation start candidate zones, the three-dimensional picture generation start candidate zone having the shallowest depth is selected as a three-dimensional picture generation start zone, and a predetermined depth inside the three-dimensional picture generation start zone is determined as a start depth of the three-dimensional picture generation; and a three-dimensional picture generator which starts the three-dimensional picture generation from the start depth of the three-dimensional picture generation determined by the start depth determiner and generates the three-dimensional picture of the ultrasonic received signal.

Also, the divider is configured to repeat a process, which obtains a voxel data column targeted for a ray-casting calculation from the three-dimensional volume data and while carrying out a cumulative addition of a product of a voxel data and a predetermined accumulation coefficient from the beginning point of the voxel data column, scans the voxel data column and when a cumulative addition value exceeds a predetermined threshold, initializes the cumulative addition value and then records a depth in the voxel data column at that time, until a voxel data column end point, and consequently divides the voxel data column, which is targeted for the ray-casting calculation, into one or a plurality of depth zones.

Also, the start depth determiner is configured to sort the one or plurality of depth zones divided by the divider in a zone length order and define the higher N (N is an integer of 1 or more) depth zones as ray-casting start candidate zones, and select the shallowest zone among the ray-casting start candidate zones as a ray-casting start zone and then determine a preset depth inside the ray-casting start zone as a ray-casting start depth.

Also, the start depth determiner is configured to sort the one or plurality of depth zones divided by the divider in the zone length order and determine the higher N (N is the integer of 1 or more) three-dimensional picture generation start candidate zones or ray-casting start candidate zones and when there is the three-dimensional picture generation start candidate zone or ray-casting start candidate zone of the preset zone length or less in the N three-dimensional picture generation start candidate zones or ray-casting start candidate zones, defines a preset position inside the zone of the shallowest depth among the three-dimensional picture generation start candidate zones or ray-casting start candidate zones except them as a three-dimensional picture generation start depth or ray-casting start depth, and when all of the N three-dimensional picture generation start candidate zones or ray-casting start candidate zones have the preset zone length or less, determine a lead position of the voxel data column targeted for the three-dimensional picture generation or ray-casting calculation as a three-dimensional picture generation start position or ray-casting start position.

Also, this is configured to further contain:

a candidate zone number setter for a user to set the number of the three-dimensional picture generation start candidate zones for the start depth determiner; and a superimposing unit for superimposing a depth color classification picture of the start depth of the three-dimensional picture generation, which is determined by the start depth determiner in accordance with the number of the three-dimensional picture generation start candidate zones set by the candidate zone number setter, on the three-dimensional picture generated by the three-dimensional picture generator.

With this configuration, independently of the turbidity degree of the amniotic fluid and the like, which exist between the three-dimensional picture generation target, such as the fetus and the like, and the portion that is not the three-dimensional picture generation target, such as the placenta or the uterine wall or the like, serving as the obstacle of the fetus, it is possible to accurately determine the three-dimensional picture generation start depth. Also, when the determined three-dimensional picture generation start depth is not located at the position desired by the user, this can be changed.

According to the present invention, independently of the turbidity degree of the amniotic fluid and the like, which exist between the three-dimensional picture generation target, such as the fetus and the like, and the portion that is not the three-dimensional picture generation target, such as the placenta or the uterine wall or the like, serving as the obstacle of the fetus, it is possible to accurately determine the three-dimensional picture generation start depth. In particular, since the integrating method is used to analyze the brightness curve, the stable solution can be obtained as compared with the conventional method of using the brightness or brightness change (differential value) as the threshold. Also, when the zone length sorting is carried out in determining the start depth, the relative nature of the division zone can be compared, thereby enabling the further stable solution to be determined.

Also, even if the calculated start depth differs from the position intended by the user, the picture on which the current start depth is colored is superimposed on the three-dimensional picture. Thus, this enables the fact that the calculated start depth differs from the position intended by the user to be easily recognized. Also, a user interface of ultrasonic diagnostic equipment is used to specify the voxel data column in which the start depth is desired to be changed and to change the start candidate zone number N. Thus, the start depth can be easily changed.

BEST MODE FOR CARRYING OUT THE INVENTION

The embodiments of the present invention will be described below with reference to the drawings.

First Embodiment

Figure 1:
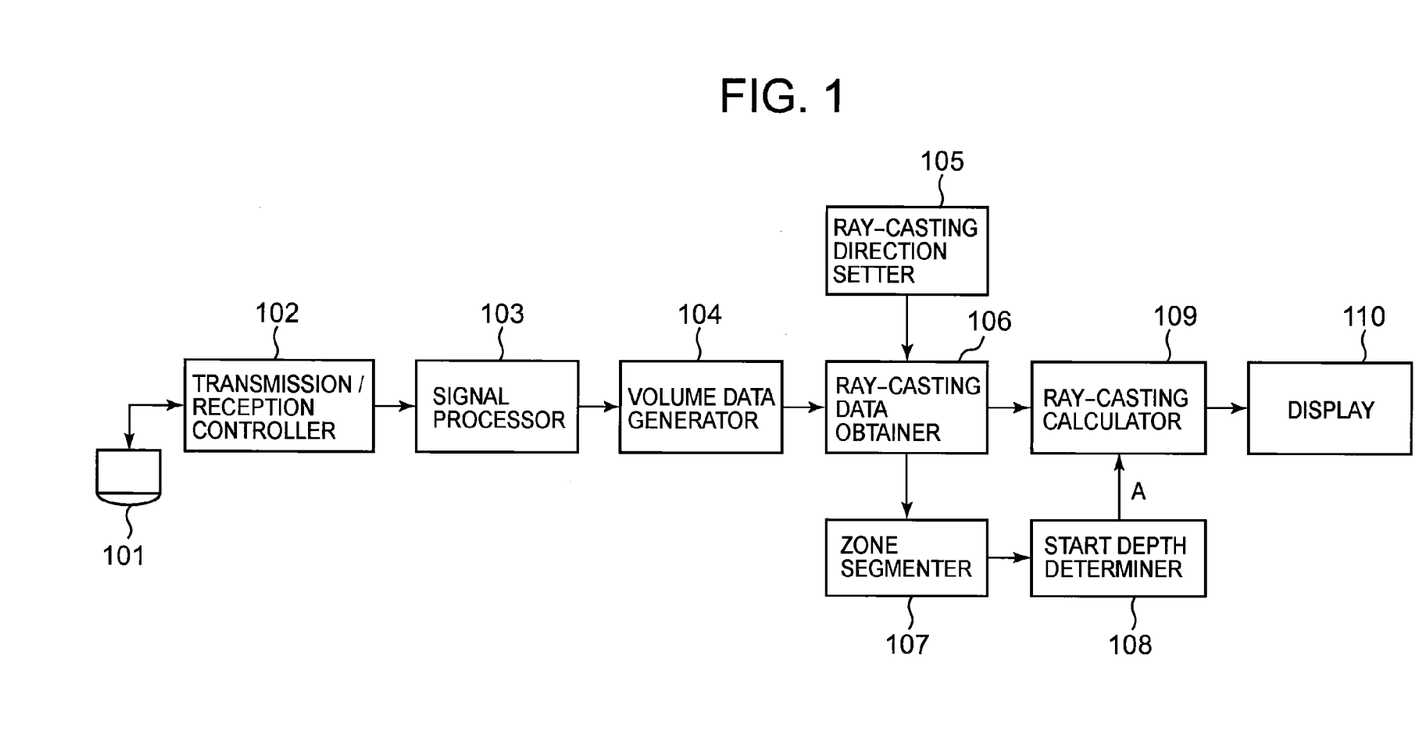
FIG. 1 is a block diagram of entire ultrasonic diagnostic equipment in a first embodiment according to the present invention.

FIG. 1 is a block diagram showing the first embodiment of three-dimensional ultrasonic picture diagnostic equipment according to the present invention. In FIG. 1, a two-dimensional array probe 101 transmits an ultrasonic beam in a two-dimensional direction to a target in contact with it and receives a reflection wave from the target. A transmission/reception controller 102 performs the transmitting/receiving direction control of the ultrasonic beam (beam forming) and the phasing addition of the received signal on the two-dimensional array probe 101 and generates a reception sound data. A signal processor 103 performs a filtering process, a detecting process and the like on the reception sound data processed by the transmission/reception controller 102. A volume data generator 104 receives the reception sound data from the signal processor 103, uses the coordinate parameters such as the shape of the two-dimensional probe 101 and the reception direction of the reception sound data and performs the coordinate conversion on a three-dimensional orthogonal coordinate system and then generates the volume data.

A ray-casting direction setter 105 determines a ray-casting direction (three-dimensional picture generation direction) for the volume data generated by the volume data generator 104, in accordance with the parameters from an input device such as a track ball or the like. A ray-casting data obtainer 106 obtains the voxel data column, which is targeted for the ray-casting, from the volume data generated by the volume data generator 104, along the ray-casting direction determined by the ray-casting direction setter 105. A divider uses an integrating method and divides the depth direction of the ultrasonic received signal into one or a plurality of depth zones so that the cumulative addition values become the approximately same values. By the way, in this embodiment, the divider is described by using a zone segmenter 107. A start depth determiner 108 analyzes the zone lengths of the division zones generated by the zone segmenter 107 and determines a ray-casting start depth A, as described later. The three-dimensional picture generator performs a ray-casting calculation process on the voxel data column obtained by the ray-casting data obtainer 106, from the ray-casting start depth A determined by the start depth determiner 108, and generates the three-dimensional picture. By the way, in the embodiment of the present invention, the three-dimensional picture generator is described by using a ray-casting calculator 109. A display 110 displays the process result of the ray-casting calculator 109 on a monitor or the like.

The operations of three-dimensional ultrasonic picture diagnostic equipment in the first embodiment according to the present invention will be described below. At first, in order to scan the object including the target, the transmission/reception controller 102 carries out the transmitting direction control (beam forming) of the ultrasonic beam. Thus, the ultrasonic beam is transmitted from the two-dimensional array probe 101 to the object. The transmitted ultrasonic beam is reflected on the sound boundary in the object and again returned to the two-dimensional array probe 101. The two-dimensional probe 101 receives a reflection wave from the object, converts the reflection wave into an electrical received signal and outputs to the transmission/reception controller 102. The transmission/reception controller 102 performs the phasing addition on the received signal from the two-dimensional array probe 101 and consequently generates the reception sound data and also adds the direction information of the transmitted/received sound beam to the reception sound data and then outputs to the signal processor 103.

The signal processor 103, after performing a band pass filtering process on the reception sound data and removing noise components, performs the detecting process and consequently extracts the power components of the reception sound data and then outputs to the volume data generator 104. The volume data generator 104 monitors the direction information of the sound beam added to the reception sound data and stores all of the reception sound data from the scanning start of the entire region of the three-dimensional object to the end thereof. When the scanning of the entire region of the object has been ended, the volume data generator 104 carries out the coordinate conversion in accordance with the coordinate parameters, such as the shape of the two-dimensional probe 101, the direction information of the sound beam added to the reception sound data and the like, and generates the three-dimensional orthogonal coordinate system volume data.

The ray-casting direction setter 105 instructs the sight line direction relative to the volume data desired by a user, by using the input device such as the track ball and the like and consequently determines the ray-casting direction relative to the volume data and then outputs to the ray-casting data obtainer 106. The ray-casting data obtainer 106 obtains the voxel data column, which is targeted for the ray-casting, from the volume data along the ray-casting direction and outputs to the zone segmenter 107 and the ray-casting calculator 109.

The zone segmenter 107, while cumulatively adding (integrally processing) the product of a voxel brightness value and a preset accumulation coefficient C from the beginning point of the voxel data column, for the voxel data column targeted for the ray-casting calculation, scans the voxel data column, and initializes the cumulative addition value to zero, when the cumulative addition value exceeds a predetermined threshold T1, and records the depth in the voxel data column at this time. This process is repeatedly performed until a voxel data end point. Consequently, the voxel data column targeted for the ray-casting calculation is divided into one or a plurality of division zones in the depth direction, and its division information is outputted to the start depth determiner 108.

The start depth determiner 108 sorts the one or plurality of division zones in an order starting with a longer zone length and determines the higher N (N is the integer of 1 or more) ray-casting start candidate zones. Next, the ray-casting candidate zone having the shallowest depth among those N ray-casting start candidate zones is selected as a ray-casting start zone S, and the preset predetermined depth inside the ray-casting start zone S is defined as a ray-casting start depth A, or when all of the higher N ray-casting start candidate zones are equal to or less than the preset zone length, the lead position of the voxel data column targeted for the ray-casting calculation is defined as the ray-casting start depth A and passed to the ray-casting calculator 109.

Here, the determining method of the final ray-casting start depth A determined by the start depth determiner 108 is calculated by using a rate coefficient α that is preset in a system. The rate coefficient α is the value that indicates the portion of the ray-casting start zone S to be set as the final ray-casting start depth A, when the length of the ray-casting start zone S is normalized to 1. Then, this is defined as the ray-casting start depth A, as follows:
If α=0.0, Lead Position Of Ray-Casting Start Zone S;
If α=0.5, Middle Position Of Ray-Casting Start Zone S; And
If α=1.0, Final Position Of Ray-Casting Start Zone S.
Next, the ray-casting calculator 109, while scanning the voxel data column from the ray-casting start depth A set by the start depth determiner 108, carries out the ray-casting calculation and consequently generates the three-dimensional picture of the object and then outputs to the display 110.

Figure 2:
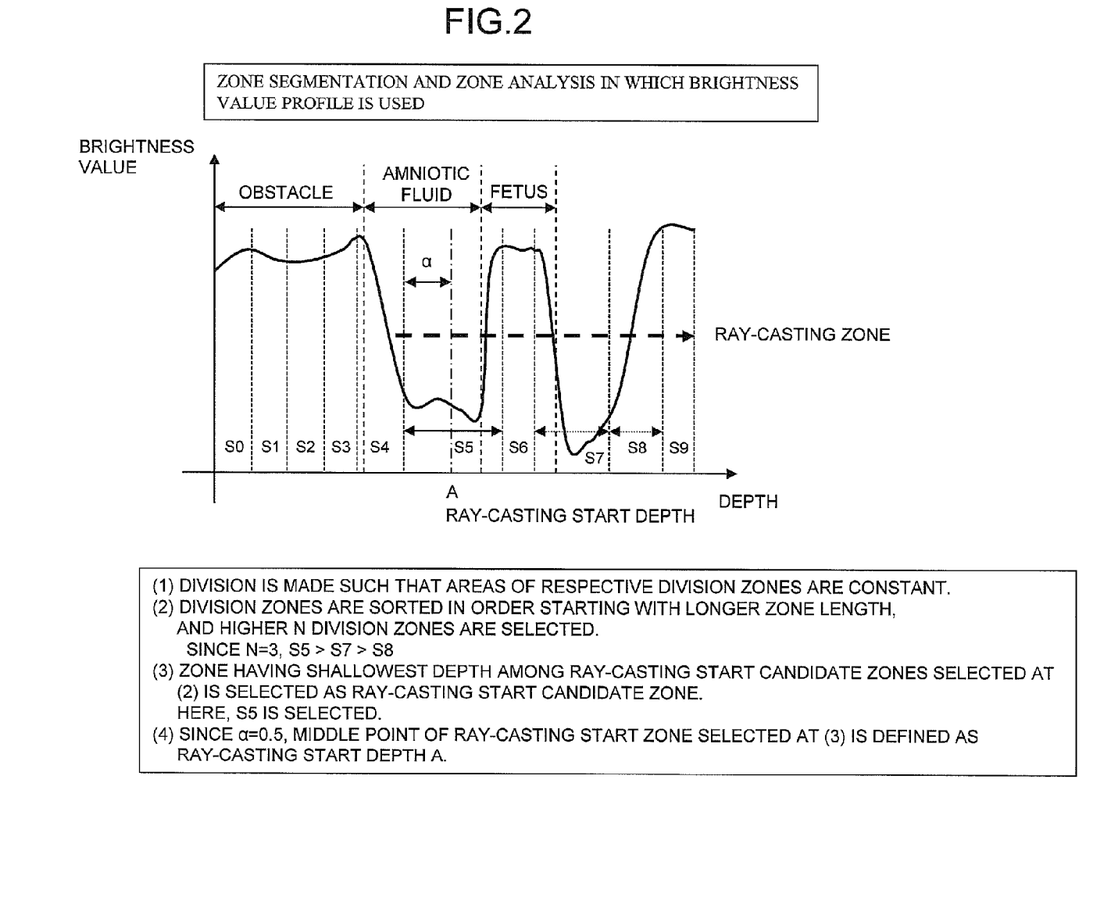
FIG. 2 is an explanatory view that shows one example of a voxel brightness value profile in the first embodiment according to the present invention and a zone segmentation and a zone analysis.

This will be described below in detail by using FIG. 2. Also, for the purpose of the easy description, the preset parameters are assumed such that the accumulation coefficient C=1, the ray-casting start candidate zone number N=3 and the rate coefficient α=0.5. The graph in FIG. 2 shows one example of the voxel brightness value profile in the depth direction relative to the voxel data column inputted from the ray-casting data obtainer 106. When for the voxel data column, it is processed by the zone segmenter 107, the depth direction is divided from a division zone S0 to a division zone S9. Here, since the accumulation coefficient C=1, each of the zone areas between the division zone S0 and the division zone S8 is approximately equal to the threshold T1. (As for the division zone S9, since there is the possibility of the arrival at the final point of the voxel data column without any conformity with the threshold T1, the zone area is not always equal to those of the division zones S0 to S8). The division zone length calculated by the start depth determiner 108 has the nature in which this is relatively long when the voxel brightness value remains low in the voxel brightness value profile, and this is relatively short when the voxel brightness value remains high. That is, the length of the division zone S5 including the amniotic fluid portion is said to be relatively longer than those of the zones S0 to S4 and S6 which include the obstacles and the fetus.

Next, the start depth determiner 108 sorts the division zones S0 to S8 divided by the zone segmenter 107 (the division zone S9 is removed from the analysis target, because its zone area is not always equal to those of the division zones S0 to S8, because of the possibility of the arrival at the final point of the voxel data column without any conformity with the threshold T1) in the order starting with the longer zone length. Here, the length of the division zone S5 that includes the amniotic fluid portion is relatively longer than those of the zones S0 to S4 and S6 that include the obstacles and the fetus. Thus, the action for sorting them in the order starting with the longer zone length is equivalent to the action for sorting them in the order starting with the division zone having the higher possibility of including the amniotic fluid zone S5.

Here, since N=3, the higher three division zones S5, S7 and S8 are selected as the ray-casting start candidate zones that include the ray-casting start depth A in the ray-casting calculator 109. Next, the three ray-casting start candidate zones S5, S7 and S8 are sorted in the depth order, and the ray-casting start candidate zone S5 having the shallowest depth is selected as the ray-casting start zone S. Then, since the rate coefficient α=0.5, the middle point in the ray-casting start zone S(=5) is determined as the ray-casting start depth A and passed to the ray-casting calculator 109. Thus, the three-dimensional picture of the fetus from which the obstacle is removed can be displayed.

According to such configuration, the zone segmenter 107 is used to divide the voxel data column into the plurality of division zones S0 to S9 in the depth direction, and the start depth determiner 108 is used to analyze the zone lengths of the division zones S0 to S9 and the depth relation between the division zones S0 and S9. Thus, the amniotic fluid portion whose zone length is long is detected, which can provide the three-dimensional picture of the fetus from which the obstacle is automatically removed.

Figure 3:
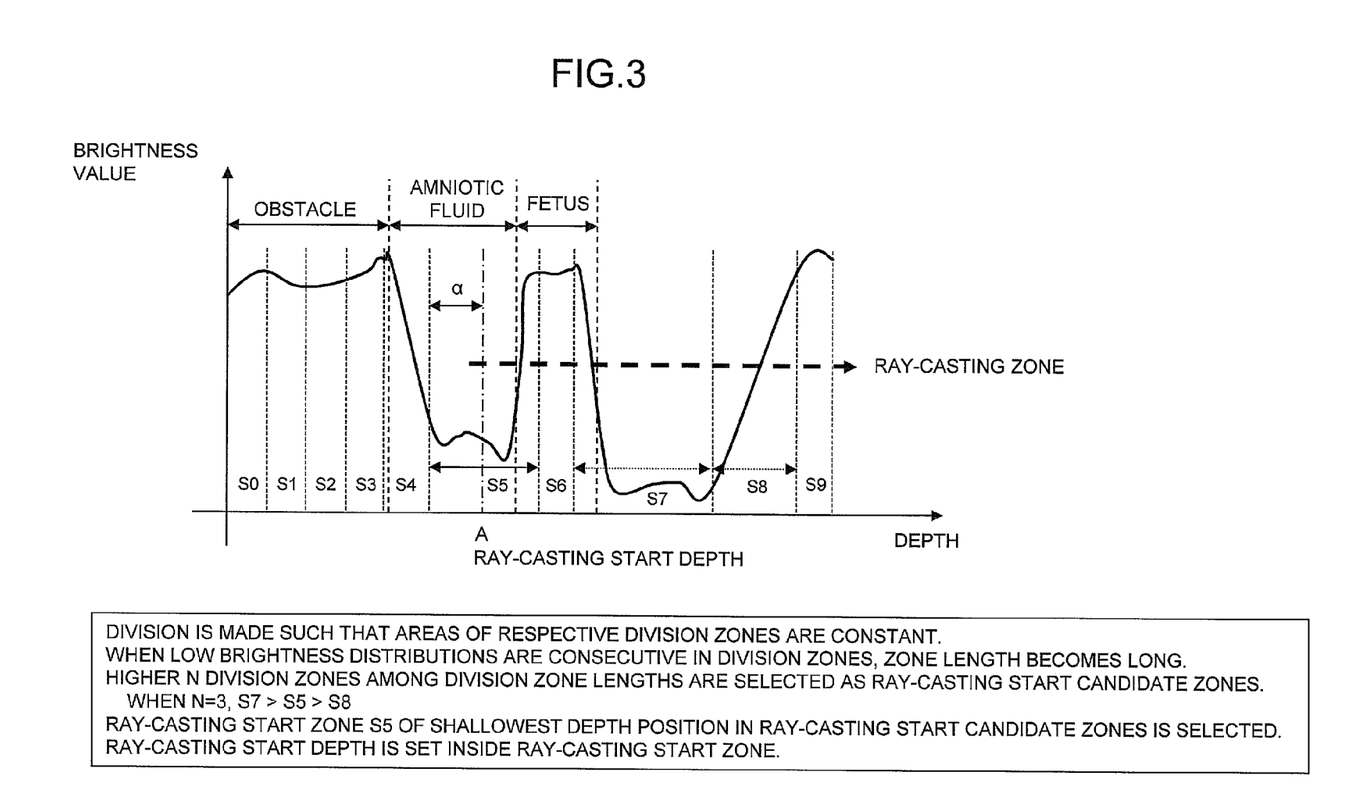
FIG. 3 is an explanatory view that shows a different example of the voxel brightness value profile in the first embodiment according to the present invention, and a zone segmentation and a zone analysis.

Next, the reason why, although [the start candidate zone having the longest zone length] is not selected, [the ray-casting start candidate zone S5 having the shallowest depth] is selected as the ray-casting start zone S is described. Here, FIG. 3 shows a different example of the voxel brightness value profile, and the brightness value of the zone S7 deeper than the zone S6 including the fetus portion is lower than that of the amniotic fluid zone S5. The zone length of the division zone S5 including the amniotic fluid portion is relatively longer than the zone length of the division zone S6 that includes the fetus portion. However, in FIG. 3, when the ray-casting start candidate zones S5, S6 and S7 are sorted in the zone length order, the relation of S7>S5>S8 is established. Here, the zone S5 of the fetus portion must be targeted for the ray-casting calculation. Thus, even if [the ray-casting start candidate zone S7 having the longest zone length] is simply defined as the ray-casting start zone S, the three-dimensional picture of the fetus cannot be generated. Thus, in order to generate the three-dimensional picture of the fetus, the candidate zone S5 is required to be selected. So, when the higher N zones after they are sorted in the zone length order and then [the ray-casting start candidate zone S5 having the shallowest depth] among them is defined as the ray-casting start zone S, the three-dimensional picture of the fetus can be generated. Here, although the N value may be the very important element, the three-dimensional structure of the fetus is relatively simple. Hence, the N value can set as the stable value except the special case.

Figure 4:
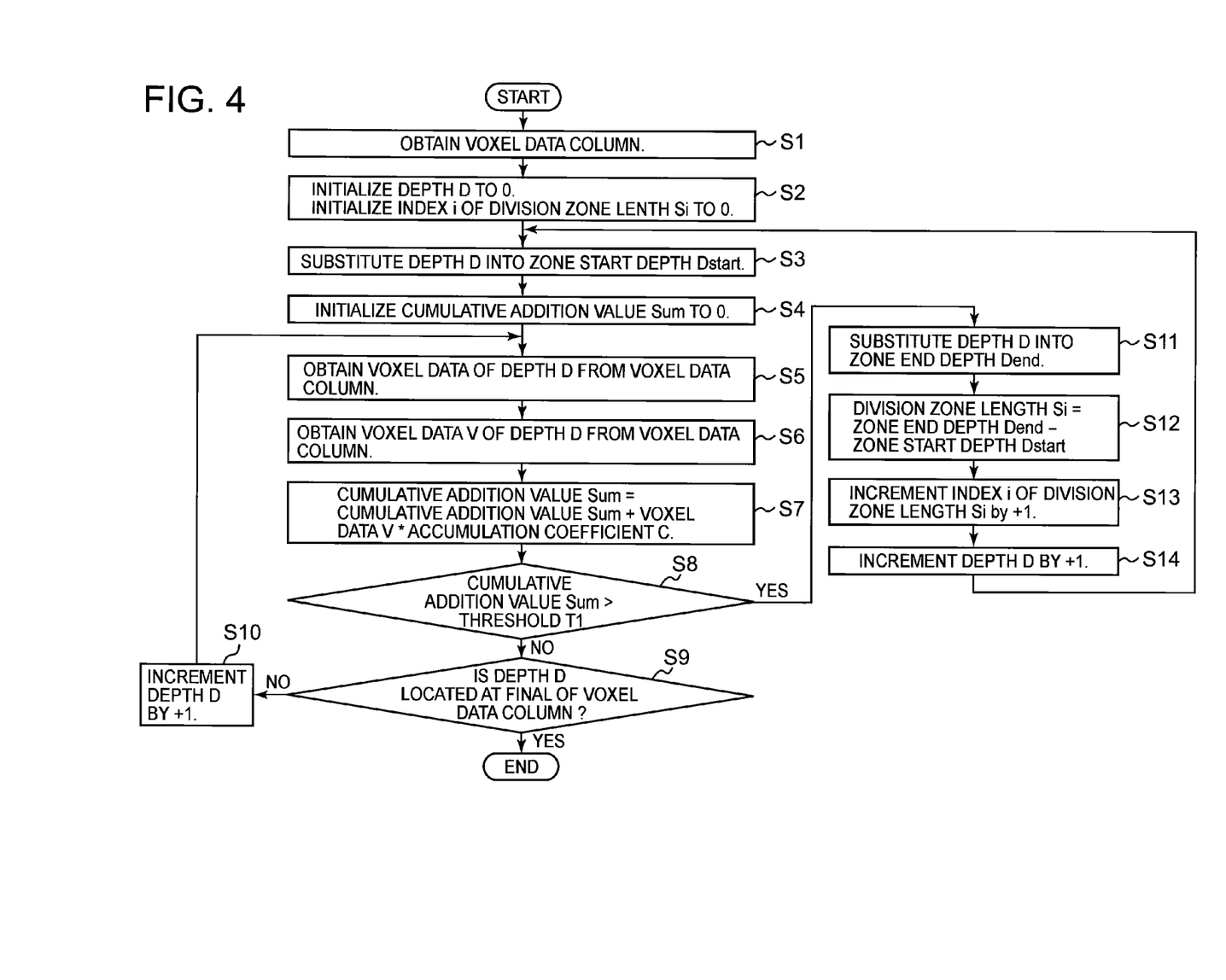
FIG. 4 is a flowchart for describing the operations of a zone segmenter in the first embodiment according to the present invention.

FIG. 4 shows a flowchart for describing the operations in the zone segmenter 107. In FIG. 4, at first, the voxel data column is obtained from the ray-casting data obtainer 106 (Step S1). Next, the depth D is initialized to 0, and an index i of a division zone length Si is initialized to 0 (Step S2). Next, the depth D is substituted into a zone start depth Dstart (Step S3). Next, a cumulative addition value Sum is initialized to 0 (Step S4). Next, the voxel data of the depth D is obtained from the voxel data column obtained at the step S1 (Step S5). Next, this is obtained as a voxel data V of the depth D (Step S6).

Next, the following value is calculated (Step S7).

Cumulative Addition Value Sum=Cumulative Addition Value Sum+Voxel Data $V$×Accumulation Coefficient $C$ Next, whether or not the cumulative addition value Sum>the threshold T1 is checked (Step S8). Then, if Sum>T1 is not established, whether or not the depth D is located at the final of the voxel data column is checked (Step S9). If this is not located at the final, the depth D is incremented by 1 (Step S10). Next, the process flow returns to the step S5, and the process for a next depth is repeated. At the step S9, if the depth D is located at the final of the voxel data column, this process is ended.

Also, at the step S8, if Sum>T1, the depth D is substituted into a zone end depth Dend (Step S11). Next, the following is calculated (Step S12).

Division Zone Length $Si$=Zone End Depth Dend− Zone Start Depth Dstart

Next, the index i of the division zone length Si is incremented by 1 (Step S13). Next, the depth D is incremented by 1 (Step S14). Next, the process flow returns to the step S3. Then, the process for a next division zone is repeated.

Figure 5:
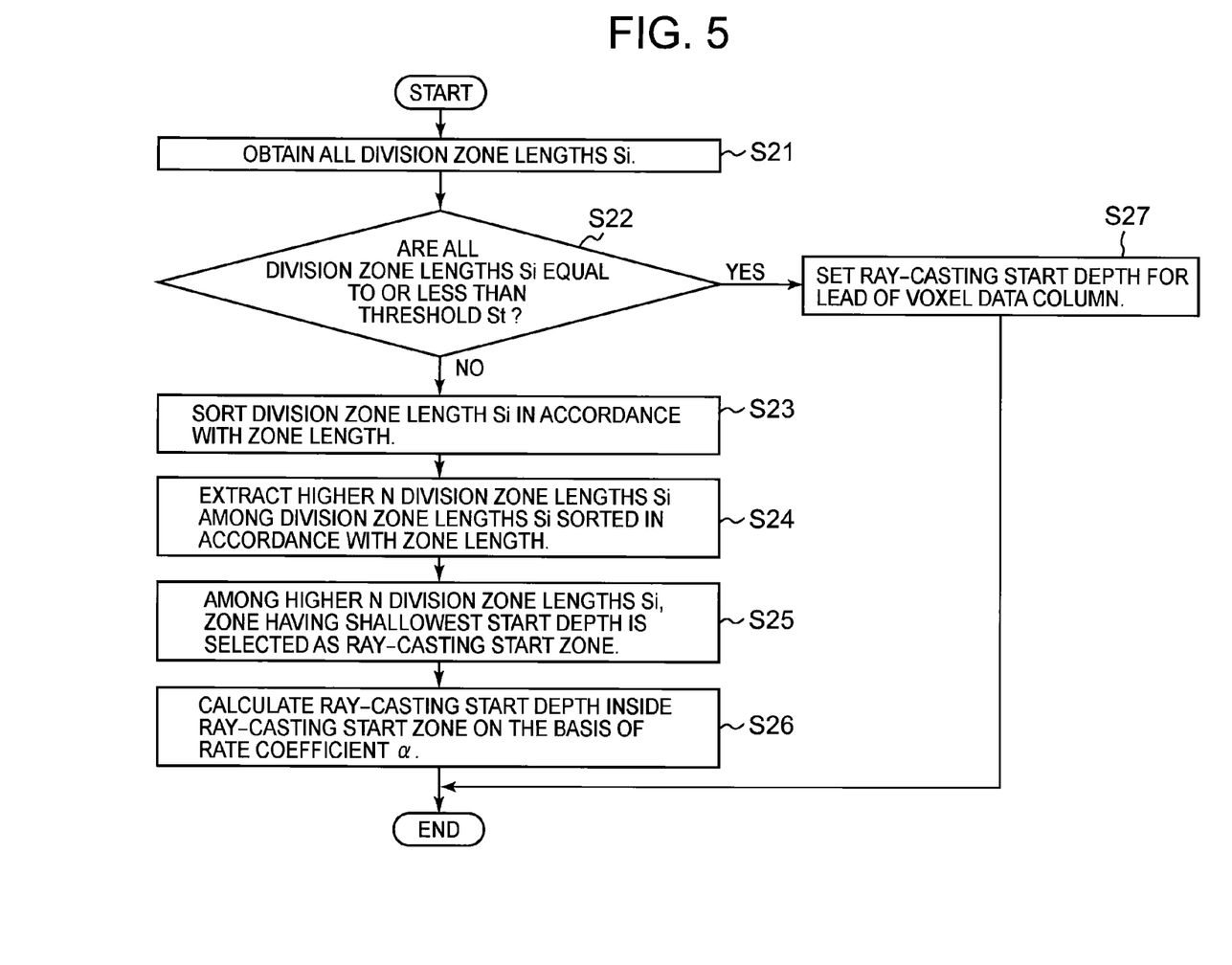
FIG. 5 is a flowchart for describing the operations of a start depth determiner in the first embodiment according to the present invention.

FIG. 5 shows a flowchart for describing the operations in the start depth determiner 108. In FIG. 5, all of the division zone lengths Si are obtained (Step S21). Next, whether or not all of the division zone lengths Si are equal to or less than a threshold St is checked (Step S22). If so, the ray-casting start depth A is set for the lead of the voxel data column (Step S27). Then, the process is ended.

On the other hand, at the step S22, if all the division zone lengths Si are not equal to or less than the threshold St, all the division zone lengths Si are sorted in accordance with the zone lengths (Step S23). Next, among the division zone lengths Si sorted in accordance with the zone lengths, the higher N ray-casting start candidate zones with regard to the zone length are extracted (Step S25). Next, among the higher N ray-casting start candidate zones with regard to the zone length, the ray-casting start candidate zone having the shallowest zone start depth Dstart is selected as the ray-casting start zone (Step S25). Next, in accordance with the rate coefficient α, the ray-casting start depth A inside the ray-casting start zone is calculated (Step S26). Then, the process is ended.

Second Embodiment

Figure 6:
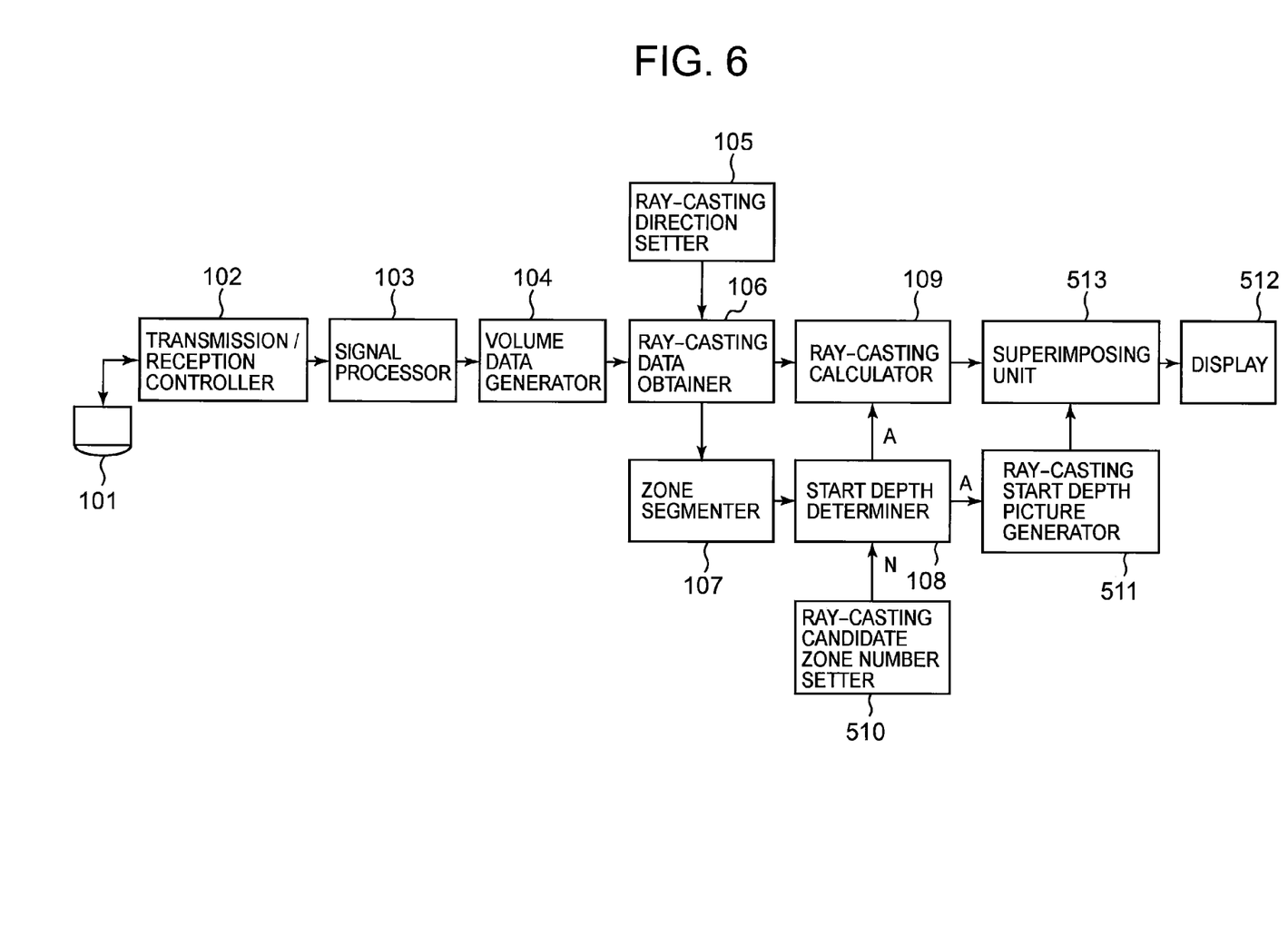
FIG. 6 is a block diagram of entire ultrasonic diagnostic equipment in a second embodiment according to the present invention.

FIG. 6 is a block diagram showing three-dimensional ultrasonic picture diagnostic equipment in the second embodiment according to the present invention. In FIG. 5, the two-dimensional array probe 101, the transmission/reception controller 102, the signal processor 103, the volume data generator 104, the ray-casting direction setter 105, the ray-casting data obtainer 106, the zone segmenter 107, the start depth determiner 108 and the ray-casting calculator 109 are equal to the configurations in FIG. 1, respectively. By using a ray-casting candidate zone number setter 510, the user sets the ray-casting candidate zone number N used by the start depth determiner 108. A ray-casting start depth picture generator 511 generates a colored picture corresponding to a ray-casting start depth P determined by the start depth determiner 108. A superimposing unit 513 generates the picture in which the three-dimensional picture generated by the ray-casting calculator 109 and the colored picture corresponding to the ray-casting start depth P generated by the ray-casting start depth picture generator 511 are superimposed. A display 512 displays the output from the superimposing unit 513.

The operations of three-dimensional ultrasonic picture diagnostic equipment in the second embodiment according to the present invention will be described below. Since the operations with regard to the obstacle removal are equal to the operations in the first embodiment according to the present invention, their operations are omitted here. Then, the operations of the ray-casting candidate zone number setter 510, the ray-casting start depth picture generator 511, the display 512 and the superimposing unit 513, which are newly added and changed, are centrally described.

At first, in a first obstacle removing operation, the ray-casting candidate zone number setter 510 sets the same ray-casting candidate zone number N=B for the start depth determiner 108, with regard to the voxel data columns targeted for all of the ray-castings, and carries out the obstacle removal. In this case, since the start depth determiner 108 calculates the ray-casting start position at the ray-casting candidate zone number N=B. Thus, by using this result, the ray-casting calculator 109 generates the three-dimensional picture. The ray-casting start depth picture generator 511 generates the colored picture corresponding to the ray-casting start depth. The superimposing unit 513 superimposes those pictures and outputs to the display 512. Here, the superimposing of the pictures implies an alpha blending displaying and implies that the colored picture corresponding to the ray-casting start depth is transparently displayed on the three-dimensional picture.

Next, the user, since viewing this superimposed picture, judges whether or not the three-dimensional picture is the picture from which the obstacle is normally removed. At this time, since the colored picture corresponding to the ray-casting start depth is superimposed, the relation between the three-dimensional picture and the ray-casting start depth can be simultaneously known, which enables the region from which the obstacle cannot be normally removed to be easily recognized.

Next, the user specifies the region, from which the obstacle cannot be normally removed, by using the pointing device such as the track ball and the like, and specifies the specified region as the region from which the obstacle cannot be normally removed and consequently passes the region information to the ray-casting candidate zone number setter 510. The ray-casting candidate zone number setter 510 changes the ray-casting candidate zone number N from B to C, with regard to the voxel data column targeted for the ray-casting which becomes inside the region, in accordance with the passed region information. The change amount is set in accordance with the parameters previously set for the system. The ray-casting candidate zone number setter 510 sets the ray-casting candidate zone number N=C relative to the voxel data column targeted for the changed ray-casting, for the start depth determiner 108. The start depth determiner 108 uses the updated ray-casting candidate zone number N=C, carries out the zone analysis and calculates the ray-casting start depth and then passes to the ray-casting calculator 109 and the ray-casting start depth picture generator 511.

Finally, the ray-casting calculator 109 generates the three-dimensional picture, and the ray-casting start depth picture generator 511 generates the colored picture corresponding to the ray-casting start depth, and the superimposing unit 513 superimposes those pictures, which are displayed on the display 512. The user, since repeating these operations, can obtain the three-dimensional picture from which the obstacles are perfectly removed.

By the way, in the first and second embodiments, as the probe for three-dimensionally scanning the object, the two-dimensional array probe 101 of the electron scanning type is used. However, instead of this two-dimensional array probe 101, a hybrid probe for mechanically driving a one-dimensional array probe or a mechanical probe for two-dimensionally driving a single probe may be used.

By the way, the first and second embodiments have been described by using the ray-casting method as the three-dimensional picture generation technique. However, the similar effect can be obtained even by using a different three-dimensional picture generation technique such as a surface rendering and the like.

By the way, the respective function blocks used in the above-mentioned embodiments are typically attained as LSIs that are integrated circuits. They are individually integrated into one chip or integrated into one chip so as to include a part or all of them. Here, it is referred to as LSI. However, it may be referred to as IC, a system LSI, a super LSI and an ultra LSI, depending on the difference of the integration degree. Also, the style of the integrated circuit is not limited to the LSI, and this may be attained as a dedicated circuit or a general processor. After the LSI is manufactured, a programmable FPGA (Field Programmable Gate Array) or a reconfigurable processor in which the connection and setting of the circuit cells inside the LSI can be re-configured may be used. Moreover, when a technique that manufactures an integrated circuit instead of the LSI due to the advancement of the semiconductor technique or the derived different technique appears, its technique can be naturally used to integrate the function blocks. For example, the application of a bio-technique and the like may be considered as the possibility.

The present invention is useful as the method that has the automatic obstacle removing function of a high precision and automatically removes the obstacles, such as the placenta and the uterine wall, which cover the fetus in the obstetrics and gynecology region and then draws only the fetus. Also, this is useful not only in the obstetrics and gynecology region but also in the other medical fields. In particular, this can be applied to even the field such as the drawing of a mitral valve inside a cardiac ventricle in a cardiovascular clinic field and the like. Moreover, with regard to the modality, this can be applied not only to ultrasonic diagnostic equipment but also to CT or MRI or the like. Moreover, this can be applied not only to the medical field but also to the industry field.

What is claimed is:

1. Ultrasonic diagnostic equipment configured to automatically determine a start depth of three-dimensional picture generation and to start three-dimensional picture generation, the ultrasonic diagnostic equipment comprising:
   a transmission/reception controller configured to control transmitting and receiving an ultrasonic signal through an ultrasonic probe;
   a divider configured to cumulate brightness values in a depth direction of an ultrasonic received signal based on the ultrasonic signal to thereby divide the depth direction of said ultrasonic received signal into a plurality of depth zones such that respective cumulative addition brightness values, respectively associated with respective depth zones, are approximately equal to a predetermined value, each depth zone of the plurality of depth zone having a zone length, along the depth direction, corresponding to a number of brightness values, which are accumulated by the divider to establish the depth zone;
   a start depth determiner configured to:
      select a user-configurable number of three-dimensional picture generation start candidate zones having the longest zone lengths among the plurality of depth zones,
      select a three-dimensional picture generation start candidate, from the user-configurable number of three-dimensional picture generation start candidate zones, having a shallowest depth along the depth direction of the received ultrasound signal, as a three-dimensional picture generation start zone, and
      determine a predetermined depth inside said three-dimensional picture generation start zone as the start depth of said three-dimensional picture generation; and
   a three-dimensional picture generator configured to start three-dimensional picture generation from the start depth of said three-dimensional picture generation start zone determined by said start depth determiner and to generate a three-dimensional picture of said ultrasonic received signal.

2. The ultrasonic diagnostic equipment according to claim 1, wherein said divider is configured to obtain a voxel data column targeted for a ray-casting calculation from three-dimensional volume data generated from said ultrasonic received signal and to repeat a process in which the divider for dividing the voxel data column into the plurality of depth zones:
   scans the voxel data column from a beginning point of the voxel data column while carrying out a cumulative addition of a product of voxel data of a voxel and a predetermined accumulation coefficient; and
   records a depth in the voxel data column when a cumulative addition value exceeds a predetermined threshold to generate a depth zone at the recorded depth and re-initializes the cumulative addition value,
   until a voxel data column end point is reached.

3. The ultrasonic diagnostic equipment according to claim 2, wherein the three-dimensional picture generator configured to carry out the ray-casting calculation to generate the three-dimensional picture of said ultrasonic received signal.

4. The ultrasonic diagnostic equipment according to claim 1, wherein said start depth determiner is further configured to:
   sort the user-configurable number of depth zones in a decreasing order according to zone length to identify a top N (N is the integer of 1 or more) three-dimensional picture generation start candidate zones or ray-casting start candidate zones in the order,
   define, when there is a three-dimensional picture generation start candidate zone or ray-casting start candidate zone smaller than a preset zone length in the top N three-dimensional picture generation start candidate zones or ray-casting start candidate zones, a preset position inside a zone having the shallowest depth among the three-dimensional picture generation start candidate zones or ray-casting start candidate zones as the three-dimensional picture generation start depth or ray-casting start depth, and determine, when all of said top N three-dimensional picture generation start candidate zones or ray-casting start candidate zones have the preset zone length or less, a lead position of the voxel data column targeted for three-dimensional picture generation or ray-casting calculation as the three-dimensional picture generation start position or ray-casting start position.

5. The ultrasonic diagnostic equipment according to claim 1, further comprising:
a candidate zone number setter configured to enable a user to set the user-configurable number of said three-dimensional picture generation start candidate zones for said start depth determiner; and
a superimposing unit configured to superimpose a depth color classification picture of the start depth of said three-dimensional picture generation, which is determined by said start depth determiner in accordance with the user-configurable number of said three-dimensional picture generation start candidate zones set by said candidate zone number setter, on the three-dimensional picture generated by said three-dimensional picture generator.

6. The ultrasonic diagnostic equipment according to claim 1, wherein the respective cumulative addition brightness values, respectively associated with respective depth zones and having approximately equal values, are computed by initializing a cumulative addition brightness value to zero at a start point and recording a depth in the received ultrasonic signal when the cumulative addition brightness value, from the start point, exceeds the predetermined value.

* * * * *